United States Patent
Matsuda (10) Patent No.: US 6,465,802 B1
(45) Date of Patent: Oct. 15, 2002

(54) PARTICLE MEASUREMENT APPARATUS FLOW CELL USEFUL FOR SAMPLE FLUIDS HAVING DIFFERENT REFRACTIVE INDEXES

(75) Inventor: Tomonobu Matsuda, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 0 days.

(21) Appl. No.: 09/528,146

(22) Filed: Mar. 17, 2000

(30) Foreign Application Priority Data

Mar. 18, 1999 (JP) .......................................... 11-073979
Jul. 6, 1999 (JP) .......................................... 11-191194

(51) Int. Cl.$^7$ .............................................. G01N 15/06
(52) U.S. Cl. ........................................ 250/574; 356/442
(58) Field of Search .............................. 250/222.2, 573, 250/574, 576; 356/436, 440, 441, 442

(56) References Cited

U.S. PATENT DOCUMENTS 5,392,114 A * 2/1995 Cole ........................... 356/338
5,416,580 A * 5/1995 Trainer ....................... 356/336
5,416,581 A * 5/1995 Kanngiesser ................. 356/343

* cited by examiner

*Primary Examiner*—Stephone Allen
*Assistant Examiner*—Bradford Hill
(74) *Attorney, Agent, or Firm*—Carrier, Blackman & Associates, P.C.; Joseph P. Carrier; William D. Blackman (57) ABSTRACT

A flow cell for obtaining information on particles suspended in sample fluid, wherein an irradiation region M is defined in the flow cell for functioning as a particle detection portion to be irradiated with a laser beam La, and a wall portion of the flow cell is so adapted and arranged that the laser beam La becomes incident upon an outer wall surface of the flow cell 1 at a predetermined angle $\theta_1$ ($\theta_1 \neq 0°$) and exits from an inner wall surface 5b of the flow cell 1 into the sample fluid 6 at a refraction angle 0°.

Further the wall portion 5 of the flow cell 1 is so arranged that the laser beam La becomes incident upon a boundary surface between the sample fluid and the opposite inner wall surface of the flow cell 1 at a predetermined incident angle $\alpha$ ($\alpha \neq 0°$) after being incident upon the sample fluid and passing through the irradiation region M.

19 Claims, 6 Drawing Sheets

PRIOR ART

FIG. 9

PRIOR ART

PARTICLE MEASUREMENT APPARATUS FLOW CELL USEFUL FOR SAMPLE FLUIDS HAVING DIFFERENT REFRACTIVE INDEXES

BACKGROUND OF THE INVENTION

1. Field of the Invention

The present invention relates to a flow cell for forming an irradiation region therein, as a particle detector portion, and to a particle measurement apparatus for obtaining particle information, including a diameter of particles and so on, which are suspended in sample fluid passing through the irradiation region by using the flow cell.

2. Description of Relevent Art

Figure 8:
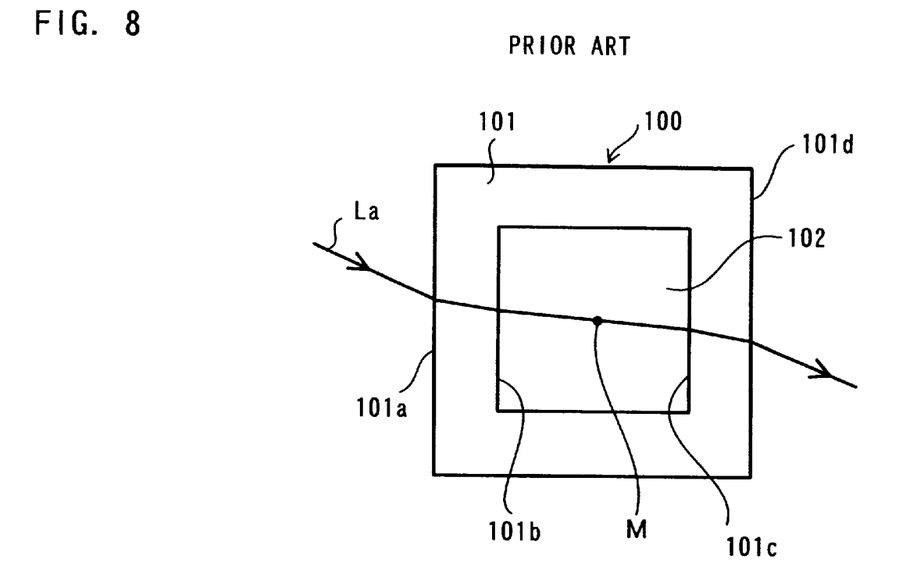
FIG. 8 shows a cross-section view of the conventional flow cell.

As shown in FIG. 8, a conventional flow cell 100 is made of a transparent material, and is constructed to have a straight flow path or passage of a predetermined length, having a square cross-section thereof. And, an outer wall surface 101a and an inner wall surface 101b of a wall portion 101, constructing the flow cell 100 through which a laser beam La passes, are formed to be parallel each other.

Figure 9:
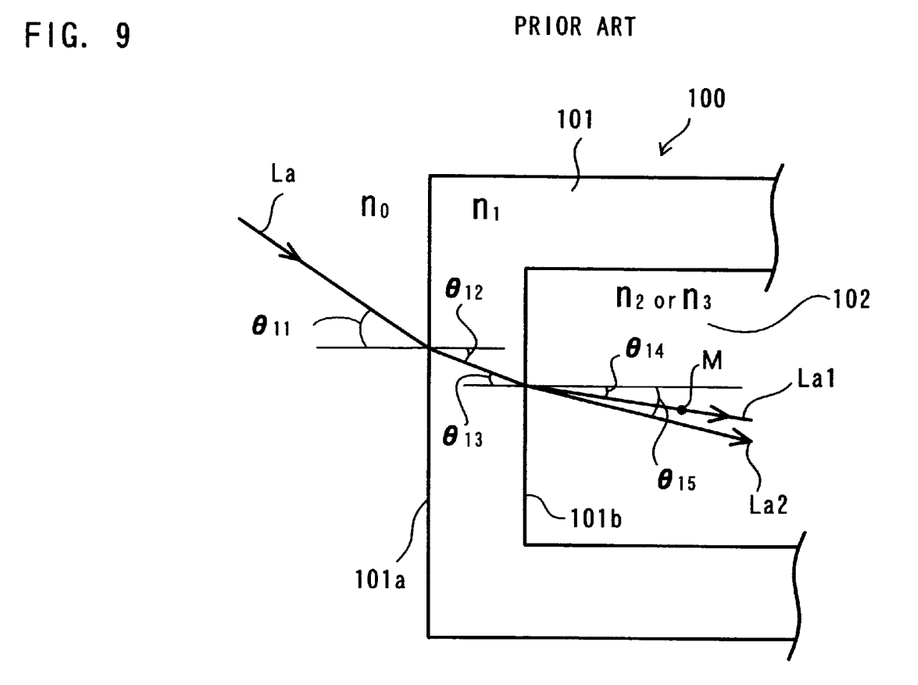
FIG. 9 shows a view for explaining a transmission path of light in a wall portion of the conventional flow cell.

Also, as shown in FIG. 9 when the laser beam La from a laser light source is irradiated upon the flow cell 100, the laser beam La is incident upon a boundary surface between air and the outer wall surface 101a at an incident angle $\theta_{11}$ ($\theta_{11} \neq 0°$) and is refracted at an refraction angle $\theta_{12}$.

This is because, when the laser beam La is incident upon the outer wall surface 101a of the flow cell 100 at right angle by setting the incident angle $\theta_{11}$ to be zero ($\theta_{11} \neq 0°$), the laser beam La is reflected on the outer wall surface 101a, so as to return a portion of the reflection light back to the laser light source. Therefore, it is prevented from superposing on the laser beam La as return or feedback noise.

However, depending on the refractive index of sample fluid 102 (i.e., a solvent of the sample fluid) flowing inside the flow cell 100, the refraction angle of the laser beam La changes at the boundary surface between the inner wall surface 101b and the sample fluid 102, therefore the laser beam La propagating within the sample fluid 102 comes to be La1 (in a case where the refractive index of the sample fluid is $n_2$) or La2 (in a case where the refractive index of the sample fluid is $n_3$). As a result of this, the irradiation region M, being provided at the center of the flow passage as the detection portion of particles, is shifted in the position thereof.

Namely, according to Snell's law, when the laser beam La is incident upon the boundary surface between the inner wall surface 101b and the sample fluid 102 at the incident angle $\theta_{13}$ (the outer wall surface 101a and the inner wall surface 101b are parallel each other, therefore $\theta_{13} = \theta_{12}$), the refraction angle comes to be $\theta_{14}$ if the refractive index of the sample fluid is $n_2$, and it comes to be $\theta_{15}$ if the refractive index of the sample fluid is $n_3$.

Then, a light collecting means, which is provided to fit to the position of the irradiation region M corresponding to the sample fluid of refractive index $n_2$, is shifted or not properly aligned in the position thereof in the case where the sample fluid has a refractive index $n_3$. In such a situation, the light collecting means cannot detect light scattered by particles passing through the irradiation region M.

Accordingly, there is a problem that particle information, including a particle diameter and so on, cannot be detected accurately, due to the the difference in the kinds of sample fluids being analyzed.

Furthermore, depending on the shape of the wall portion 101 constructing the flow cell 100, the laser beam La passing through the irradiation region M is reflected on the boundary surface between the sample fluid 102 and the inner wall surface 101c and/or between the outer wall surface 101d and air, to be turned or reflected back toward the laser light source in a part thereof. Therefore, there are problems that the portion of the reflection light superposes on the laser beam La as feedback noise, and that the portion of the reflection light passes through the irradiation region M again, thereby increasing noise.

SUMMARY OF THE INVENTION

According to the present invention, for overcoming the problems mentioned above, there is provided a flow cell for obtaining particle information, including a diameter of particles and so on, suspended in sample fluid, wherein an irradiation region, through which the sample fluid passes, is defined in said flow cell for functioning as a detection portion to be irradiated with light, and a wall portion of said flow cell is so adapted and arranged that when said light is incident upon an outer wall surface of the flow cell at a predetermined incident angle $\theta$ ($\theta \neq 0°$), said light exits from an inner wall surface into said sample fluid at a refraction angle of almost or approximately 0°.

With this flow cell and arrangement according to the invention, it is possible to keep the irradiation region functioning as a particle detection portion at a constant position, independent of and influence by a value or magnitude of refractive index of the sample fluid.

Further, according to the present invention, there is also provided a flow cell for obtaining particle information, including a diameter of particles, suspended in sample fluid, wherein an irradiation region, through which the sample fluid passes, is defined in said flow cell for functioning as a detection portion to be irradiated with light, and a wall portion of said flow cell is so adapted and arranged that said light becomes incident upon a boundary surface between said sample fluid and an inner wall surface of the flow cell at a predetermined incident angle $\alpha$ ($\alpha \neq 0°$) after being passing through said irradiation region.

With this flow cell and arrangement according to the invention, after light passes through the irradiation region functioning as a particle detection portion, the light can be prevented from being reflected on the boundary surface between the sample fluid and the inner wall surface back into a direction of the light source, independent of and influence by a value or magnitude of refractive index of the sample fluid. This advantageously prevents superposing of the feedback noise onto the light due to self action a portion of the light, as well as avoiding an increase of the noise due to the portion of reflection light passing through the irradiation region again.

It is preferable that, in the flow cell as defined above, the wall portion of the flow cell is so arranged that the light is incident upon a boundary surface between an outer wall surface of the flow cell and air at a predetermined incident angle $\alpha'$ ($\alpha' \neq 0°$).

With this additional feature, after light passes through the irradiation region functioning as a particle detection portion, the light can be prevented from being reflected on the boundary surface between the sample fluid and the inner wall surface into a direction of, the light source, independent of any influence by a value or magnitude of the refractive index of the sample fluid, and in addition, the light can also be prevented from being reflected on the boundary surface between the outer wall surface and air back into a direction reflected portion of the the light source, superposing of the feedback noise onto the light due to turn-back of light, as well as avoiding an increase of the noise due to the portion of reflection light passing through the irradiation region again.

Furthermore, according to the present invention, there is also provided a flow cell for obtaining particle information, including a diameter of particles, suspended in sample fluid, wherein an irradiation region, through which the sample fluid passes, is defined in said flow cell for functioning as a detection portion to be irradiated with light, and a wall portion of said flow cell is so adapted and arranged that said light becomes incident upon a boundary surface between said sample fluid and an inner wall surface of the flow cell at approximately 0°, and then becomes incident upon a boundary surface between an outer wall surface of the flow cell and air at a predetermined incident angle $\alpha''$ ($\alpha'' \neq 0°$) after passing through said irradiation region.

With this flow cell and arrangement according to the invention, it is possible to prevent the light from being reflected on the boundary surface between the outer wall surface and air back into a direction of the light source, thereby preventing superposing of the feedback noise onto the light due to a reflected portion of the light, as well as avoiding an increase of the noise due to the portion of reflection light passing through the irradiation region again.

And, according to the present invention, there is further provided a particle measurement apparatus, comprising: a flow cell as described above; a light source for irradiating light upon a passage of said flow cell, so as to form an irradiation region; and an optical detection process means for detecting and processing scattered light, transmission light and/or diffraction light caused by particles within said irradiation region.

With this apparatus according to the invention, it is possible to measure the number or diameter of the particles suspended in the sample fluid, independent of a value or magnitude in the refractive index of the sample fluid.

DETAILED DESCRIPTION OF PREFERRED EMBODIMENT(S)

Hereinafter, embodiments according to the present invention will be fully explained by referring to the attached drawings.

Figure 1:
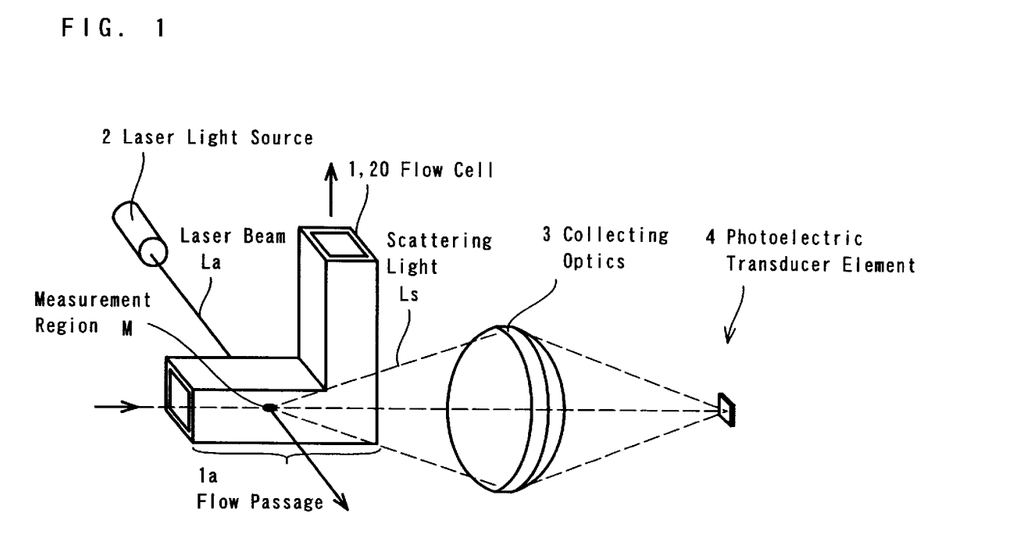
FIG. 1 shows the construction of a particle measurement apparatus according to the present.

A particle measurement apparatus according to the present invention, as shown in FIG. 1, comprises a flow cell 1, a laser light source 2, collecting optics 3, a photoelectric transducer element 4, and so on. The flow cell 1 is made of a transparent material, having a straight flow passage 1a of a predetermined length, and it is bent in a "L"-shaped cylinder as a whole.

Figure 2:
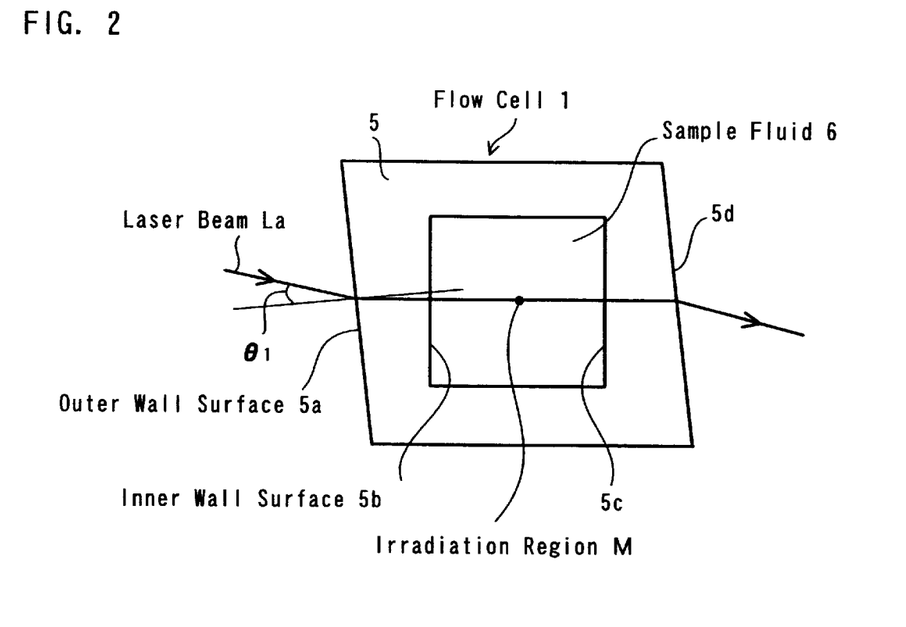
FIG. 2 shows a cross-section view of a flow cell according to the first embodiment of the present invention.

Also, the flow cell, according to the first embodiment of the present invention, is constructed of a wall portion 5 having a quadrilateral shape in the cross-section thereof, as shown in FIG. 2. The cross-section of an inner periphery thereof is square in shape while the cross-section of an outside thereof is a parallelogram in shape.

Accordingly, an outer wall surface 5a upon which a laser beam La is incident and an inner wall surface 5b from which the laser beam La exits are not parallel each other, but instead the outer wall surface 5a defines a predetermined angle (inclination) with respect to the inner wall surface 5b. In the same manner, an opposite inner wall surface 5c upon which the laser beam La is incident and an outer wall surface 5d from which the laser beam La exits outside are not parallel each other, but instead the outer wall surface 5d defines a predetermined angle (inclination) with respect to the inner wall surface 5c.

Again referring to FIG. 1, a straight flow passage 1a of a predetermined length is provided in order to bring sample fluid 6 into laminar flow when it flows through the flow cell 1. As conditions for obtaining laminar flow, a viscosity of the sample fluid 6, a length of the straight flow passage, a cross-sectional shape of the flow passage, velocity of the fluid, and so on can be listed. The length of the straight flow passage 1a and the cross-sectional shape of the flow passage are determined by taking the viscosity of the sample fluid 6 and the velocity of the fluid into consideration.

A laser light source 2 irradiates the laser beam La at a redetermined position in the straight flow passage 1a of the flow cell 1, thereby forming an irradiation or measurement region M. Here, within the straight flow passage 1a, an optical axis of the laser light La meets a center axis of the straight flow passage at almost or approximately a right angle.

As shown in the FIG. 2, the laser beam La is incident upon the outer wall surface 5a at an incident angle $\theta_1$. This prevents a portion of the reflection light of the laser beam La, which is reflected on the outer wall surface 5a of the flow cell 1, from turning back in the direction of the laser beam source 2. If the portion of the reflection light is returned in the direction of the light source, the feed back noise is superposed on the laser beam La, and this is undesirable.

The collecting optics 3 have an optical axis which is coincident with the central axis of the straight flow passage 1a of the flow cell 1, and a function of collecting the scattering scattered light Ls generated from particles irradiated by the laser beam La within the irradiation region M. However, it is not always necessary that the collecting optics 3 are provided or positioned on the central axis of the straight flow passage 1a of the flow cell 1.

The photoelectric transducer element 4 is provide on the optical axis of the collecting optics 3. This photoelectric transducer element 4 transduces the scattered light Ls, which is generated from particles passing through the irradiation region M, into voltage.

Further, means in a downstream direction of this collecting optics 3 are collectively called an optical detection process means.

Explanation will be given on the function of the flow cell 1 according to the first embodiment of the present invention and a particle measurement apparatus using same.

Here, it is defined that a refractive index of air is $n_0$, a refractive index of the wall portion 5 of the flow cell 1 is $n_1$, and a refractive index of the sample fluid 6 is $n_2$ or $n_3$.

Figure 3:
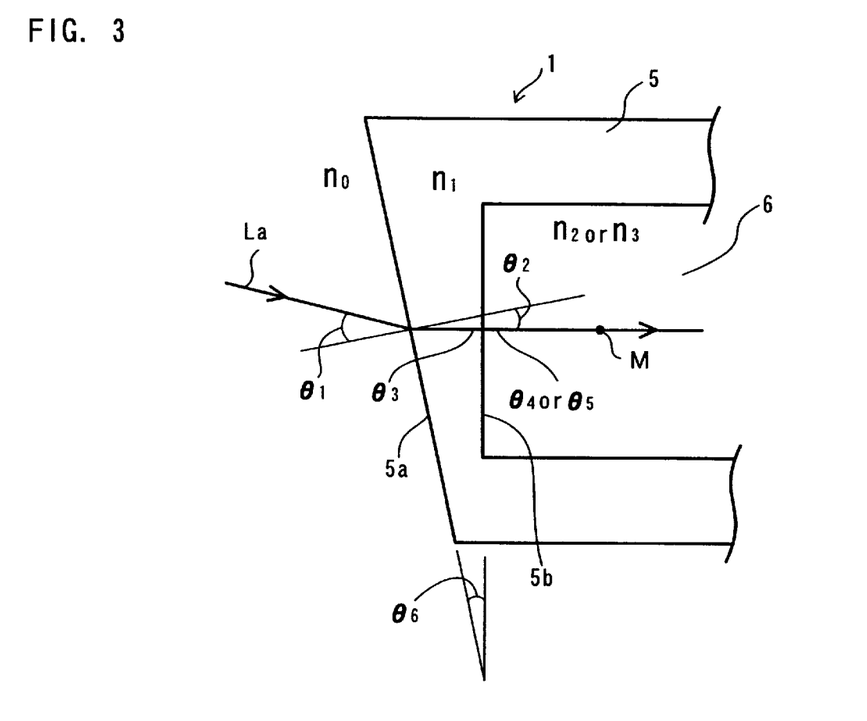
FIG. 3 shows a view for explaining a transmission path of light in a wall portion of the flow cell according to the first embodiment of the present invention.

As shown in FIG. 3, when the laser beam La emitted from the laser beam source 2 is incident upon the boundary surface between air and the outer wall surface 5a and is refracted there, it follows Snell's Law.

According to the Snell's Law, following equation (1) is established between an incident angle $\theta_1$ and a refraction angle $\theta_2$.

$$n_0 \cdot \sin \theta_1 = n_1 \cdot \sin \theta_2 \quad (1)$$

Next, the laser beam La goes straight forwards within the wall portion 5. On the boundary surface between the inner wall surface 5b and the sample fluid 6, an equation (2) shown below is established between an incident angle $\theta_3$ and a refraction angle $\theta_4$ of the sample fluid 6 having the refractive index $n_2$, or between an incident angle $\theta_3$ and a refraction angle $\theta_5$ of the sample fluid 6 having the refractive index $n_3$, in the same manner according to Snell's Law.

$$n_1 \cdot \sin \theta_3 = n_2 \cdot \sin \theta_4 = n_3 \cdot \sin \theta_5 \quad (2)$$

Accordingly, for keeping the position of the irradiation region M constant, independent of the values of the refractive index of the sample fluid 6 (i.e., $n_2$ or $n_3$), the refractive angles are to be almost equal to each other. From the equation (2), for satisfying that condition, it is sufficient to satisfy the requirement $\sin \theta_3 = \sin \theta_4 = \sin \theta_5 = 0$, i.e., that the laser beam La is incident upon the boundary surface between the inner wall surface 5b and the sample fluid 6 at an incident angle $\theta_3 = 0°$.

In such case, the required refraction angle $\theta_4$=refraction angle $\theta_5 = 0°$, i.e., that the laser beam La propagates within the sample fluid 6 always at an equal refraction angle (0°) is satisfied. However, it is not necessary that the angle $\theta_3$ is strictly 0°, and it may have a value in so far as the shift in the position of the irradiation region M is confined within permissible limits. Accordingly, it is sufficient that the angle $\theta_3$ be almost or nearly equal to 0°.

Then, in order to make the laser beam La incident upon the boundary surface between the inner wall surface 5b and the sample fluid 6 at the incident angle $\theta_3 = 0°$, in a case where the angle defined between the outer wall surface 5a and the inner wall surface 5b is $\theta_6$ as shown in the FIG. 3, it is sufficient to make the refraction angle $\theta_2$ on the boundary surface between air and the outer wall surface 5a equal to the angle $\theta_6$ (i.e., $\theta_2 = \theta_6$).

Further, in a case of setting $\theta_2 = \theta_6$ in the equation (1), the incident angle $\theta_1$ at which the laser beam La is (should be) incident upon the boundary surface between air and the outer wall surface 5a is found as follows:

The incident angle $\theta_1$ is determined by the refractive index $n_0$ of air, the refractive index $n_1$ of the wall portion 5 of the flow cell 1 and the angle $\theta_6$ defined between the outer wall surface 5a and the inner wall surface 5b, and it comes to be shown by the following equation.

$$\theta_1 = \sin^{-1}\{(n_1/n_0)\sin \theta_6\} \quad (3)$$

Accordingly, if the laser beam La is incident upon the boundary surface between air and the outer wall surface 5a at the angle $\theta_1$ satisfying the equation (3), it is possible to keep the irradiation region M at a constant position independent of the value of the refractive index of the sample fluid 6.

When the sample fluid 6 flows through the flow cell 1 mentioned above, the laser beam La is irradiated upon particles passing through the irradiation region M, and the scattered light Ls generated from the particles is collected by the collecting optics 3.

Next, the scattered light Ls collected by the collecting optics 3 is transduced into a voltage. The number or concentration of the particles is measured by the number of peaks of the voltage transduced by the photoelectric transducer element 4, and the particle diameter of the particles is measured by the value or level of the voltage.

Figure 4:
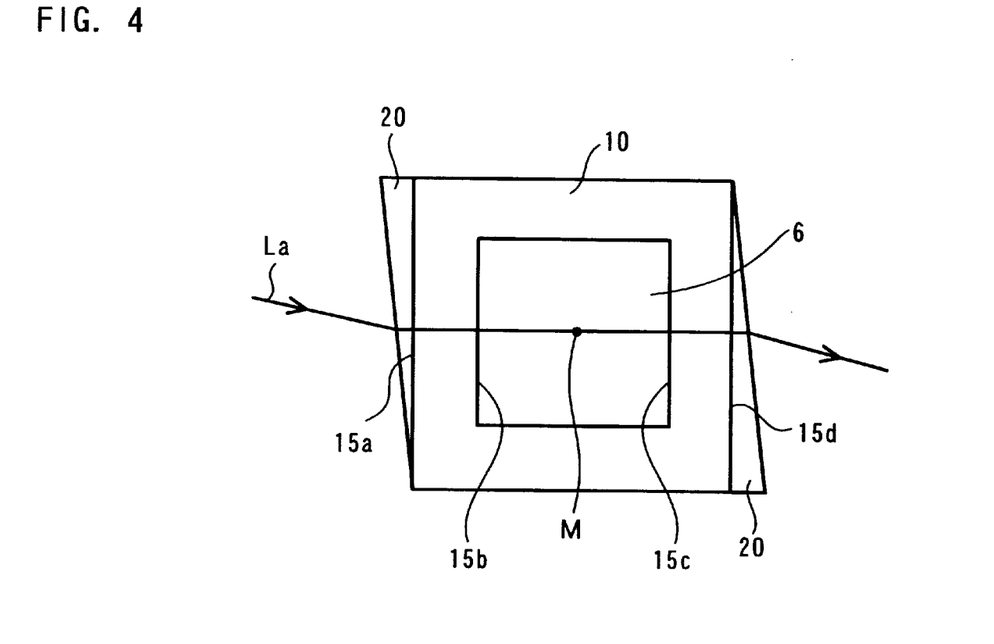
FIG. 4 shows a cross-section view of a flow cell according to the second embodiment of the present invention.

The flow cell 1, according to the first embodiment of the present invention, is formed as one body or unit. However, in as the second embodiment of the present invention shown in FIG. 4, a flow cell can be obtained by forming a flow cell 10 with an outer wall surface 15a and an inner wall surface 15b, and another outer wall surface 15d and another inner wall surface 15c, each pair of which is parallel each other, and then by attaching or bonding members 20 made of the same material as the flow cell and in a shape of a triangular prism or pillar to the outer wall surfaces 15a and 15d respectively.

Figure 5:
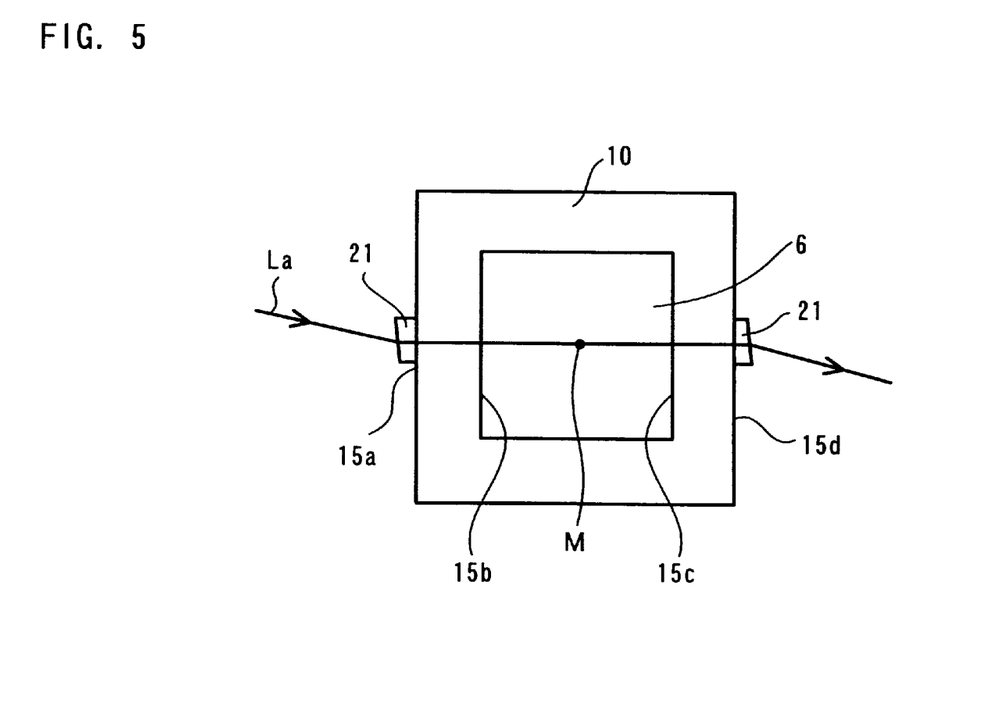
FIG. 5 shows a cross-section view of a flow cell according to the third embodiment of the present invention.

As the third embodiment shown in FIG. 5, it is also possible to make one small portion of each of the outer wall surfaces 15a and 15d have the necessary shape not parallel to the inner wall surfaces 15b, 15c, respectively, through which the laser beam La passes, by attaching or bonding members 21 with non-parallel outer surfaces and made of the same material as the flow cell to the outer wall surfaces 15a and 15d respectively.

In the first embodiment of the flow cell according to the present invention, as shown in the FIG. 2, regarding the wall portion 5 of the flow cell 1, an angle defined between the outer wall surface 5a and the inner wall surface 5b is made equal to an angle defined between the outer wall surface 5d and the inner wall surface 5c in symmetry, thereby preventing the laser beam La from turning reflecting or back along the light path by reflecting on the boundary surface between the outer wall surface 5d and air.

By the way, the form of the angle between the inner wall surface 5c and the outer wall surface 5d of the flow cell, from which the laser beam La exits, should not be restricted to the embodiments of the present invention. Namely, it is sufficient that the laser beam La can pass through the irradiation region M of the flow cell 1 with certainty independent of the sample fluid 6 flowing through the flow cell 1.

Accordingly, the inner wall surfaces 5c and 5b need be not parallel each other, and the outer wall surfaces 5a and 5d need be not parallel each other.

Figure 6:
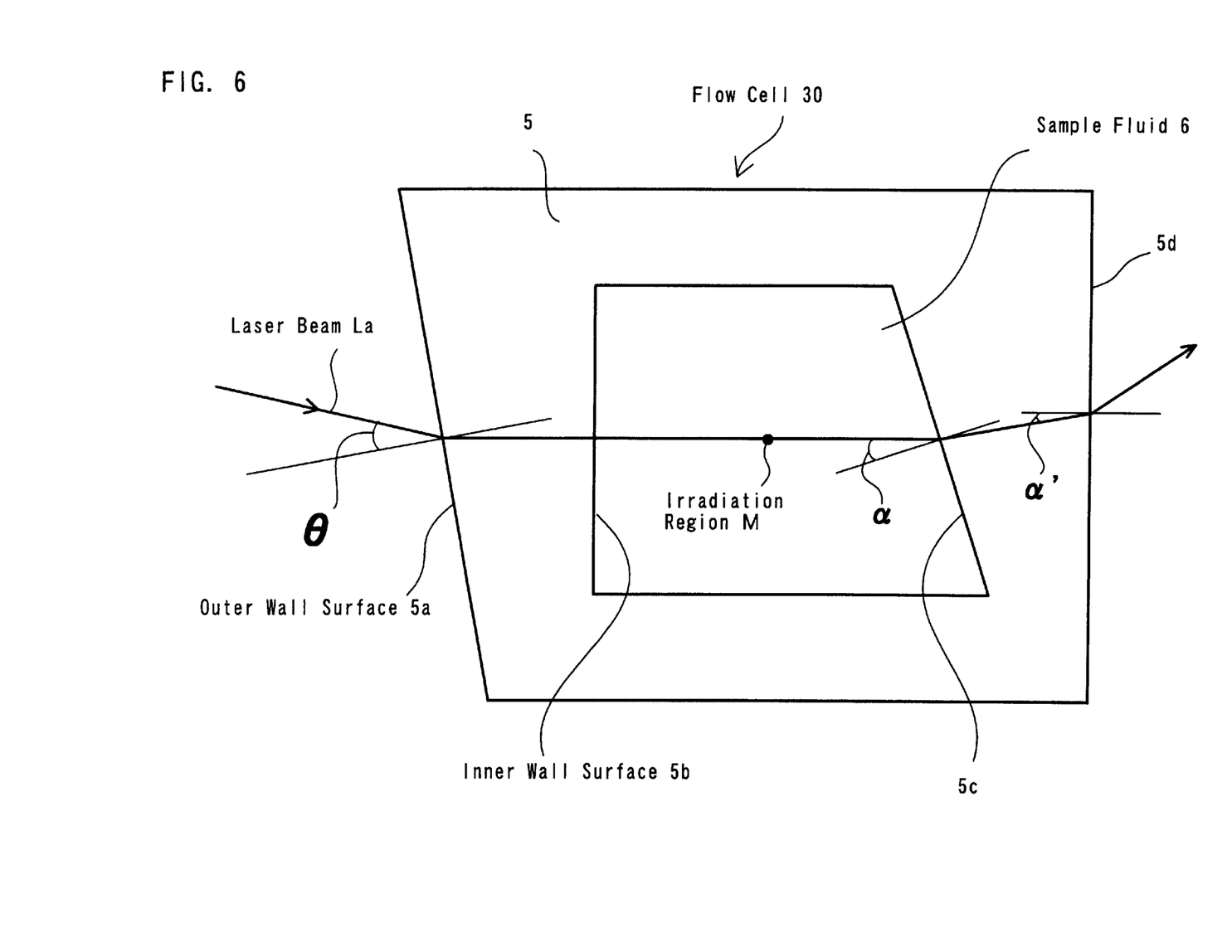
FIG. 6 shows a cross-section view of a flow cell according to the fourth embodiment of the present invention.

Next, a flow cell 30, according to the fourth embodiment of the present invention, has a wall portion 5 of a quadrilateral shape in the cross-section thereof, as shown in FIG. 6. The shapes in the cross-section of an inner periphery and an outer periphery thereof are both trapezoidal.

The outer wall surface 5a upon which the laser beam La is incident and the inner wall surface 5b from which the laser beam La exits are not parallel each other. The outer wall surface 5a is formed to define a predetermined angle (i.e., inclination) with respect to the inner wall surface 5b.

Further, the inner wall surface 5b from which the laser beam 1a exits and the inner wall surface 5c upon which the laser beam La is incident are not parallel each other. The inner wall surface 5c is formed to define a predetermined angle (i.e., inclination) with respect to the inner wall surface 5b.

As shown in the FIG. 6, the laser beam La is incident upon the boundary surface between air and the outer wall surface 5a at an incident angle $\theta$. This is because a portion of the reflection light of the laser beam La, which is reflected on the boundary surface between air and the outer wall surface 5a, is prevented from reflecting or turning back in the direction of the laser beam source 2, as mentioned above. If the portion of the reflection light is returned, the feed back noise is superposed on the laser beam La, and this is undesirable.

Further, the laser beam La passing through the irradiation region M is incident upon the boundary surface between the sample fluid 6 and the inner wall surface 5c at an incident angle α ($\alpha \neq 0°$), and then it is incident upon the boundary surface between the outer wall surface 5d and air at another incident angle α' ($\alpha' \neq 0°$)

The incident angles α and α' of the laser beam La are not 0°. This is because a portion the reflection light of the laser beam La, which is reflected on the boundary surface between the sample fluid 6 and the inner wall surface 5c on and the boundary surface between the outer wall surface 5d and air, is prevented from reflecting or turning back in the direction of the laser beam source 2, and passing through the irradiation region M again.

If the portion of the reflection light is reflected back in the direction of the source 2, the feedback noise is superposed on the laser beam La, and this is undesirable. If the portion of the reflection light passes through the irradiation region M again, noises are increased, and this is also undesirable.

Explanation will be given on the function of the flow cell according to the fourth embodiment of the present invention and the particle measurement apparatus using same.

Figure 7:
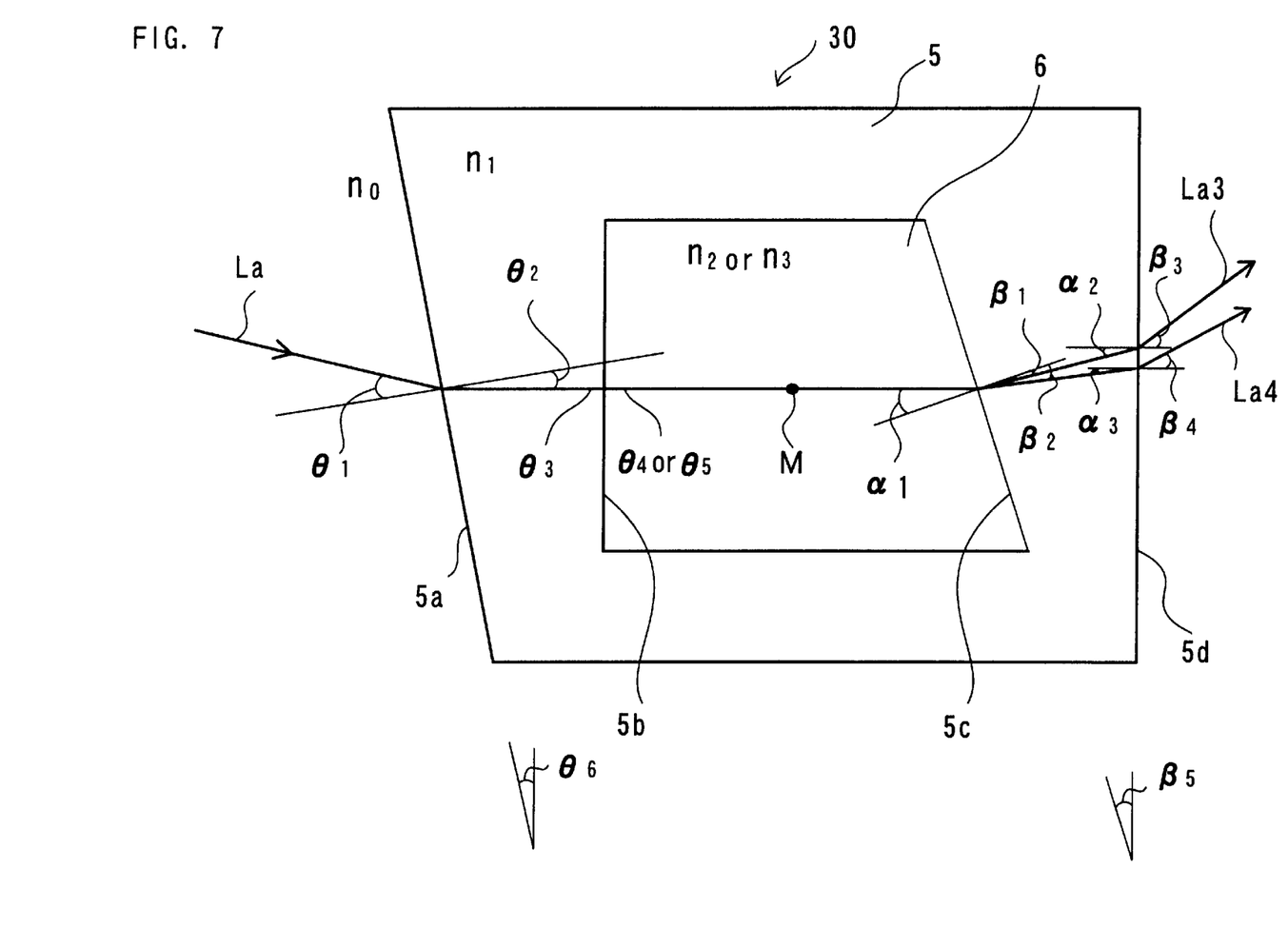
FIG. 7 shows a view for explaining a transmission path of light in a wall portion of the flow cell according to the fourth embodiment of the present invention.

However, as shown in FIG. 7, the function in the fourth embodiment up to where the laser beam La emitted from the laser light source 2 passes through the irradiation region M, is same as the function in the embodiment shown in the FIG. 3. Therefore the explanation is omitted.

When the laser beam La, which is emitted from the laser light source 2 and passes through the irradiation region M, is incident upon the boundary surface between the sample fluid 6 of the refractive index $n_2$ and the inner wall surface 5c and is refracted thereon, the following equation (4) is established between the incident angle $\alpha_1$ ($\alpha_1 \neq 0°$) and the refraction angle $\beta_1$ according to Snell's law.

$$n_2 \cdot \sin \alpha_1 = n_1 \cdot \sin \beta_1 \tag{4}$$

When the laser beam La, which passes through the irradiation region M, is incident upon the boundary surface between the sample fluid 6 of the refractive index $n_3$ and the inner wall surface 5c and is refracted thereon in the same manner, the following equation (5) is established between the incident angle $\alpha_1$ ($\alpha_1 \neq 0°$) and the refraction angle $\beta_2$ according to Snell's law.

$$n_3 \cdot \sin \alpha_1 = n_1 \cdot \sin \beta_2 \tag{5}$$

The incident angle is not 0° ($\alpha_1 \neq 0°$). This is because the boundary surface between the sample fluid 6 and the inner wall surface 5c upon which the laser beam La is incident is not parallel to the boundary surface between the inner wall surface 5b and the sample fluid 6, in which the refraction angles $\theta_4$ and $\theta_5$ come to be 0°.

Namely, this is because the wall portion 5 of the flow cell is so formed that the inner walls 5c and 5b define a predetermined angle therebetween.

When the laser beam La3 refracted at a refraction angle $\beta_1$ is incident upon the boundary surface between the outer wall surfaces 5d and air, and is refracted thereon, the following equation (6) is established between the incident angle $\alpha_2$ ($\alpha_2 \neq 0°$) and the refraction angle $\beta_3$, according to Snell's law.

$$n_1 \cdot \sin \alpha_2 = n_0 \cdot \sin \beta_3 \tag{6}$$

When a laser beam La4 refracted at a refraction angle $\beta_2$ is incident upon the boundary surface between the outer wall surface 5d and air, the following equation (7) is established between the incident angle $\alpha_3$ ($\alpha_3 \neq 0°$) and the refraction angle $\beta_4$, according to Snell's law.

$$n_1 \cdot \sin \alpha_3 = n_0 \cdot \sin \beta_4 \tag{7}$$

However, it is preferable that the incident angles $\alpha_2$ and $\alpha_3$ are set to be smaller than a critical angle ($\sin^{-1}(n_0/n_1)$) determined by the refractive indices $n_0$ and $n_1$.

This is because, if the incident angles $\alpha_2$ and $\alpha_3$ are larger than the critical angle, the laser beams La3 and La4 are undesirably bent by a total internal reflection on the boundary surface between the outer wall surface 5d and air.

Here, in a case where the angle $\beta_5$, defined between the inner wall surface 5c and the outer wall surface 5d, is equal to the refraction angles $\beta_1$ and $\beta_2$ respectively ($\beta_5 = \beta_1$, $\beta_5 = \beta_2$), the incident angles $\alpha_2$ and $\alpha_3$ come to be 0°.

The refraction angles $\beta_1$ and $\beta_2$ can be found by the following equations (8) and (9) respectively.

$$\beta_1 = \sin^{-1}\{(n_2/n_1)\sin \alpha_1\} \tag{8}$$

$$\beta_2 = \sin^{-1}\{(n_3/n_1)\sin \alpha_1\} \tag{9}$$

Accordingly, in order to prevent the incident angles $\alpha_2$ and $\alpha_3$ from being 0°, the wall portion 5 may be formed so that the angle $\beta_5$ defined between the inner wall surface 5c and the outer wall surface 5d is not equal to the refraction angles $\beta_1$ and $\beta_2$.

Here, when a condition that the incident angles $\alpha_2$ and $\alpha_3$ are not 0°, independent of the refractive indices of the flow cell 30 and the sample fluid 6, is found from the equations mentioned above, the conditions $\beta_1 \neq 0°$ and $\beta_2 \neq 0°$ can be obtained.

To satisfy the conditions on which the incident angles $\alpha_2$ and $\alpha_3$ are not 0°, i.e., $\beta_5 \neq \beta_1$ and $\beta_5 \neq \beta_2$, $\beta_5 = 0°$ is obtained.

This condition $\beta_5 = 0°$, means that the inner wall surface 5c and the outer wall surface 5d of the flow cell 30 are parallel each other. If the inner wall surface 5c and the outer wall surface 5d are formed to be parallel, the angle at which the laser beam La is incident upon the boundary surface between the outer wall surface 5d and air is not 0° independent of the refractive indices of the flow cell 30 and the sample fluid 6.

The forms, such as an angle $\beta_5$ defined between the inner wall surface 5c and the outer wall surface 5d of the flow cell 30 from which the laser beam La exits, need not be restricted to the disclosed embodiments of the present invention. According to the present invention, it is sufficient for the wall portion 5 of the flow cell 30 to be formed in which the laser beam La can pass through the irradiation region M of the flow cell 30 with certainty independent of the refractive index of the sample fluid 6 flowing through the flow cell 30, and further it is incident upon the boundary surface between the sample fluid 6 and the inner wall surface 5c at a predetermined incident angle α($\alpha \neq 0°$) and upon the boundary surface between the outer wall surface 5d and air at a predetermined incident angle α'($\alpha' \neq 0°$).

Accordingly, the forms, such as an angle $\beta_5$ between the inner wall surface 5c and the outer wall surface 5d of the flow cell 30, may need not be same with respect to the entire inner wall surface 5c and the outer wall surface 5d, as shown in the FIGS. 2 and 3. A flow cell according to the invention can be formed so that the incident angle is not 0° only in a portion where the laser beam La passes through a wall surface thereof.

Up to this point, the explanation has been given on the assumption that the laser beam La is incident upon the boundary surface between the sample fluid 6 and the inner wall surface 5c at a predetermined incident angle α (α≠0°), and that the reflection light is prevented from reflecting or turning back in the direction of the laser light source or the irradiation region M.

However, if the portion of reflected light can be reduced as small as possible, it is apparent that the advantages effect corresponding to this can be obtained.

Even if the laser beam La is incident upon the boundary surface between the sample fluid 6 and the inner wall surface 5c at the incident angle α which is 0°, it is possible to prevent the laser beam La from being reflected on the boundary surface between the outer wall surface 5d and air by forming the wall portion 5 of the flow cell 30 so that the laser beam La is incident upon the boundary surface between the outer wall surface 5d and air at a predetermined incident angle α" (α"≠0°). This advantageously prevents superposing of the feedback noise onto the laser beam La due to reflection or turn-back of a portion of the light.

In the above embodiments of the present invention, the explanation has been given on a light scattering type particle measurement apparatus. However, the present invention also can be applied to other apparatuses, such as a light intercepting type particle measurement apparatus, in which a decrease amount in a transmission light is detected due to the existence of particles which pass through the irradiation region M, so as to measure the number, the particle diameter and so on thereof, or a light diffraction type particle measurement apparatus, in which the diffraction light is detected due to the existence of particles passing through the irradiation region M.

The scope of the invention is indicated by the appended claims.

What is claimed is:

1. A flow cell for obtaining particle information, including a diameter of particles suspended in sample fluid, wherein:
   an irradiation region, through which said sample fluid passes, is defined in said flow cell for functioning as a particle detection portion to be irradiated with light; and
   a wall portion of said flow cell is so adapted and arranged that when light is incident upon an outer wall surface of said flow cell at a predetermined incident angle θ (θ≠0°), said light exits from an inner wall surface of said flow cell into said sample fluid at a refraction angle of approximately 0°.

2. A flow cell as defined in the claim 1, wherein:
   said outer wall surface and said inner wall surface of said wall portion are parallel each other; and
   a member made of material having a refractive index substantially the same as said wall portion, and in a shape of a triangular prism or pillar is bonded to said outer wall surface.

3. A flow cell as defined in the claim 1, wherein:
   said outer wall surface and said inner wall surface of said wall portion are parallel each other; and
   a member made of material having a refractive index substantially the same as said wall portion is bonded to said outer wall surface, said member covering only a portion of said outer wall portion, through which the light passes, and said member having an outer wall surface which extends non-parallel to said inner wall surface of the flow cell.

4. A flow cell for obtaining particle information, including a diameter of particles suspended in a sample fluid, wherein:
   an irradiation region, through which said sample fluid passes, is defined in said flow cell for functioning as a particle detection portion to be irradiated with light; and
   a wall portion of said flow cell is so adapted and arranged that said light becomes incident upon a boundary surface between said sample fluid and an inner wall surface of said flow cell at a predetermined incident angle α (α≠0°) after passing through said irradiation region at an angle of approximately 0°.

5. A flow cell as defined in the claim 4, wherein said wall portion of said flow cell is so adapted and arranged that said light also becomes incident upon a boundary surface between an outer wall surface of said flow cell and air at a predetermined incident angle α' (α'≠0°) different than said predetermined incident angle α, after passing through said irradiation region and said wall portion.

6. A flow cell as defined in claim 1, wherein said particle detecting portion of said flow cell remains the same when said flow cell is used for obtaining particle information of sample fluids having different refractive indexes.

7. A flow cell as defined in claim 1, wherein said sample fluid is a liquid.

8. A flow cell as defined in claim 1, wherein:
   said outer wall surface of said flow cell and said inner wall surface of said flow cell extend non-parallel to each other.

9. A flow cell as defined in claim 1, wherein:
   said wall portion of said flow cell is further adapted and arranged that said light becomes incident upon a boundary surface between said sample fluid and another inner wall surface of said flow cell at a predetermined incident angle α (α≠0°) after passing through said irradiation region.

10. A flow cell as defined in claim 1, wherein:
    said wall portion of said flow cell is further adapted and arranged that said light becomes incident upon a boundary surface between said sample fluid and another inner wall surface of said flow cell at approximately 0°, and then becomes incident upon a boundary surface between another outer wall surface of said flow cell and air at a predetermined incident angle α" (α"≠0°) after passing through said irradiation region.

11. A flow cell for obtaining particle information, including a diameter of particles suspended in sample fluid, wherein:
    an irradiation region, through which said sample fluid passes, is defined in said flow cell for functioning as a particle detection portion to be irradiated with light; and
    a wall portion of said flow cell is so adapted and arranged that said light becomes incident upon a boundary surface between said sample fluid and an inner wall surface of said flow cell at approximately 0°, and then becomes incident upon a boundary surface between an outer wall surface of said flow cell and air at a predetermined incident angle α" (α"≠0°) after passing through said irradiation region.

12. A flow cell as defined in claim 11, wherein:
    said outer wall surface of said flow cell and said inner wall surface of said flow cell extend non-parallel to each other.

13. A particle measurement apparatus, comprising:
    a flow cell;
    a light source for irradiating light upon a passage of said flow cell, so as to form an irradiation region; and
    an optical detection process means for detecting and processing scattered light, transmitted light or diffracted light by particles within said irradiation region;
    said flow cell having a wall portion so adapted and arranged that when said light is incident upon an outer wall surface of said flow cell at a predetermined incident angle θ (θ≠0°), said light exits from an inner wall surface of said flow cell into said sample fluid at a refraction angle of approximately 0°.

14. A particle measurement apparatus as defined in claim 13, wherein:

said wall portion of said flow cell is further adapted and arranged that said light becomes incident upon a boundary surface between said sample fluid and another inner wall surface of said flow cell at a predetermined incident angle α (α≠0°) after passing through said irradiation region.

15. A particle measurement apparatus as defined in claim 13, wherein:

said wall portion of said flow cell is further adapted and arranged that said light becomes incident upon a boundary surface between said sample fluid and another inner wall surface of said flow cell at approximately 0°, and then becomes incident upon a boundary surface between another outer wall surface of said flow cell and air at a predetermined incident angle α" (α"≠0°) after passing through said irradiation region.

16. A particle measurement apparatus as defined in the claim 13, wherein:

said outer wall surface and said inner wall surface of said wall portion are parallel each other; and a member made of material having a refractive index substantially the same as said wall portion, and in a shape of a triangular prism or pillar is bonded to said outer wall surface.

17. A particle measurement apparatus as defined in the claim 13, wherein:

said outer wall surface and said inner wall surface of said wall portion are parallel each other; and a member made of material having a refractive index substantially the same as said wall portion is bonded to said outer wall surface, said member covering only a portion of said outer wall portion, through which the light passes, and said member having an outer wall surface which extends non-parallel to said inner wall surface of the flow cell.

18. A particle measurement apparatus as defined in claim 13, wherein said irradiation region functions as a particle detecting portion of said flow cell, and said particle detecting portion remains the same when said flow cell is used for obtaining particle information of sample fluids having different refractive indexes.

19. A particle measurement apparatus as defined in claim 13, wherein said sample fluid is a liquid.

* * * * *

UNITED STATES PATENT AND TRADEMARK OFFICE
CERTIFICATE OF CORRECTION

PATENT NO.       : 6,465,802 B1
DATED            : October 15, 2002
INVENTOR(S)      : Tomonobu Matsuda It is certified that error appears in the above-identified patent and that said Letters Patent is hereby corrected as shown below:

Title page,
Item [57], ABSTRACT,
Lines 10-15, should follow immediately after the period at the end of line 9, so the ABSTRACT is all one paragraph;
Line 10, after "Further" insert a comma.

Column 1,
Line 14, change "Relevent" to -- Relevant --.
Line 22, after "FIG 9" insert a comma.
Line 26, change "an refraction" to -- a refraction --.
Line 28, change "at right" to -- at a right --.
Line 29, change "($\theta_{11} \neq 0°$)" to -- ($\theta_{11} = 0°$) --.
Line 64, change "the the difference" to -- differences --.

Column 2,
Line 6, before "portion" insert -- reflected --; delete "reflection".
Line 27, change "and influence" to -- any influence --.
Line 31, after "particles" delete the comma.
Line 39, delete "being".
Line 46, change "and influence" to -- any influence --.
Line 48, change "the feed-" to -- feed- --.
Line 49, change "self action" to -- reflection of --.
Line 62, after "surface" insert -- back --; after "of" delete the comma.
Line 66, after "direction" insert -- of --.
Line 67, change "reflected portion of the light source, superposing of the" to -- the light source. Again, this advantageously prevents superposing of the --.

Column 3,
Line 1, change "turn-back of light" to -- a reflected portion of the light --.
Line 7, after "particles" delete the comma.
Line 42, change "present;" to -- present invention; --.

Column 4,
Line 35, change "redetermined" to -- predetermined --.
Line 52, after "scattering" insert -- or --.
Line 57, change "provide" to -- provided --.

Column 5,
Line 8, change "the Snell's Law, following" to -- Snell's Law, the following --.

Column 6,
Line 12, change "in as" to -- in --.
Line 35, change "turning reflecting or" to -- reflecting or turning --.

UNITED STATES PATENT AND TRADEMARK OFFICE
CERTIFICATE OF CORRECTION

PATENT NO. : 6,465,802 B1
DATED : October 15, 2002
INVENTOR(S) : Tomonobu Matsuda It is certified that error appears in the above-identified patent and that said Letters Patent is hereby corrected as shown below:

Column 6, cont'd
Line 60, change "1$a$" to -- La --.

Column 7,
Line 5, change "returned" to -- reflected back toward the source 2 --.
Line 14, after "portion" insert -- of --.
Line 16, delete "on".
Line 17, after "and" insert -- on --.
Lines 26 and 58, after "cell" insert -- 30 --.

Column 8,
Line 6, equation (7), change "$n_1 \cdot \sin\alpha_3 n_0 \cdot \sin\beta_4$" to -- $n_1 \cdot \sin\alpha_3 = n_0 \cdot \sin\beta_4$ --.
Line 21, equation (8), change "$\sin^{31\ 1}$" to -- $\sin^{-1}$ --.
Line 36, after "condition" insert a comma.
Line 60, delete "may".

Column 9,
Line 7, change "advantages" to -- advantageous --.
Line 40, before "light" insert -- said --.
Line 42, change "$(\theta \neq 0°)_1$" to -- $(\theta \neq 0°),$ --.

Column 10,
Line 11, change "than" to -- from --.

Signed and Sealed this

Twenty-fourth Day of June, 2003

JAMES E. ROGAN
*Director of the United States Patent and Trademark Office*